United States Patent [19]

Galkin et al.

[11] 4,270,051

[45] May 26, 1981

[54] DEVICE FOR GAUGING THICKNESS OF REFRACTORY LINING

[76] Inventors: Jury M. Galkin, ulitsa Frunze, 67, kv. 29; Albert B. Saulin, ulitsa Studencheskaya, 52a, kv. 7; Jury N. Olshvang, ulitsa Belinskogo, 220/3, kv. 7, all of Sverdlovsk, U.S.S.R.

[21] Appl. No.: 35,052

[22] Filed: May 1, 1979

[51] Int. Cl.³ .................................................. G01N 23/00
[52] U.S. Cl. ................................. 250/358 R; 250/390; 250/392
[58] Field of Search .................. 250/358 R, 359, 360, 250/390, 391, 392

[56] References Cited

U.S. PATENT DOCUMENTS

| | | | |
|---|---|---|---|
| 2,967,937 | 1/1961 | McKay | 250/390 X |
| 3,315,076 | 4/1967 | Jordan | 250/252 |
| 3,524,062 | 8/1970 | Rocoplan et al. | 250/390 |

FOREIGN PATENT DOCUMENTS 444051 1/1973 U.S.S.R.

OTHER PUBLICATIONS

Textbook by Smolyak and Dekhtyareva, *Controls of Refractory Lining of Metallurgical Plants*, 1977.
Les Applications des Troceurs Radioactifs dans l'Utilisation des Refractaires.

*Primary Examiner*—Davis L. Willis
*Attorney, Agent, or Firm*—Fleit & Jacobson

[57] ABSTRACT

A device for gauging the thickness of refractory lining, comprising an electric pulse measuring unit connected to a lining thickness pulse transducer. The latter is mounted on that portion of the lining which is subjected to thickness measurements, and comprises a fast neutron source, a protective shield, and a thermal and epithermal neutron detector; these are successively arranged in a sealed housing. The thermal and epithermal neutron detector contains a plurality of thermal neutron counters with the number thereof being determined by the activity of the fast neutron source, and a neutron moderator intended to expand the energy interval of neutrons counted by the thermal neutron counters.

13 Claims, 3 Drawing Figures

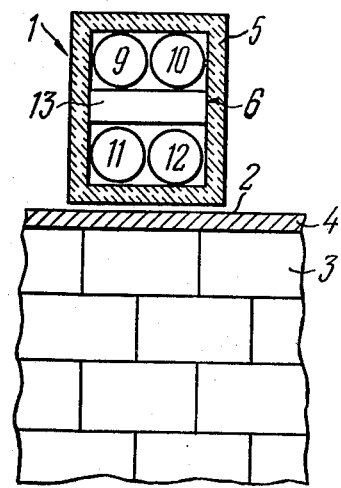
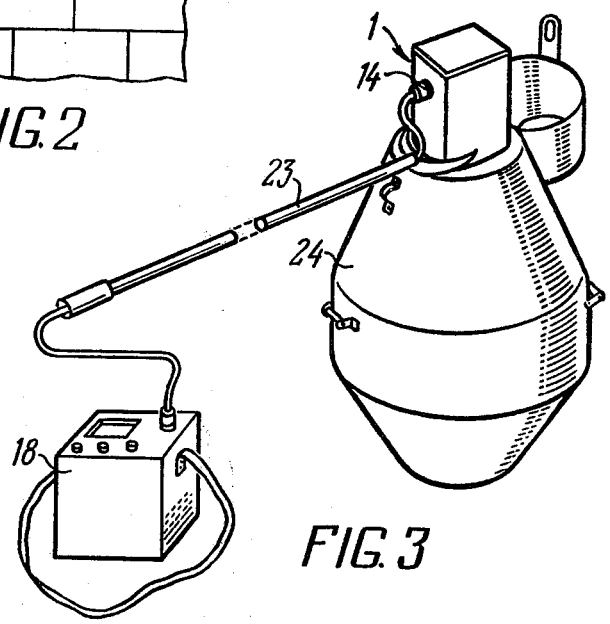
FIG. 2
FIG. 3

DEVICE FOR GAUGING THICKNESS OF REFRACTORY LINING

FIELD OF THE INVENTION

The present invention relates to means for controlling high-temperature thermal processes and, more specifically, to a device for gauging the thickness of refractory lining.

The invention is advantageous in a number of fields, such as metallurgy, the chemical industry and the production of building materials and ceramics. It is also applicable to gauging the thickness of the lining of steel-making and calcining furnaces without discontinuing their operation.

BACKGROUND OF THE INVENTION

Heating plant employed in different industries tends to operate at increasingly growing temperatures, which imposes stringent requirements on the methods of controlling the state of lining in the course of operation so as to obtain exact information on the span of trouble-free operation of each individual unit.

There is known a device for gauging the thickness of refractory lining (cf. U.S. Pat. No. 3,315,076, cl. 250-83,3, of 1967), comprising a lining thickness pulse transducer mounted on that portion of the lining which is subjected to thickness measurements. The transducer incorporates a fast neutron source, an ionizing radiation detector, and a protective shield interposed between the source and the detector. The source, shield and detector are accommodated in a sealed housing. The device further includes an electric pulse measuring unit connected to the lining thickness pulse transducer. The ionizing radiation detector is a spectrometer-type gamma ray detector. The device under review is disadvantageous in that the gamma radiation is largely absorbed by the lining material, which affects the accuracy of measurements in the case of thick linings.

In addition, the small cross-section of activation and radiative capture of neutrons by atomic nuclei of elements contained in refractory lining materials call for a fast neutron source capable of producing a neutron flux of about $10^5$ to $10^6$ neutron/cm$^2$·sec on the lining surface. To comply with this requirement, one must use complicated equipment and unwieldy biological protection shields.

The device in question is further disadvantageous in that the spectometer-type gamma radiation detector can operate only within a relatively narrow range of temperatures; this accounts for the complicated design of the lining thickness pulse transducer, as well as for difficulties involved in arranging the transducer on the lining of an operating unit.

SUMMARY OF THE INVENTION

It is an object of the present invention to provide a device for measuring the thickness of refractory lining, which would make it possible to carry out measurements within a broad range of thicknesses.

It is another object of the invention to improve the accuracy of lining thickness measurements.

It is still another object of the invention to reduce the activity level required of the fast neutron source.

The foregoing and other objects of the present invention are attained by providing a device for gauging the thickness of refractory lining, comprising a lining thickness pulse transducer mounted on that portion of the lining which is subjected to thickness measurements and including a sealed housing which accommodates a fast neutron source, an ionizing radiation detector and a protective shield interposed between them, the device further including an electric pulse measuring unit connected to the lining thickness pulse transducer and being characterized in that the ionizing radiation detector of the lining thickness pulse transducer is a thermal and epithermal neutron detector incorporating thermal neutron counters the number of which is determined by the activity of the fast neutron source, and a neutron moderator intended to expand the energy interval of neutrons counted by the thermal neutron counters.

The fast neutron source is preferably mounted on the wall of the sealed housing of the lining thickness pulse transducer, which immediately adjoins the portion of the lining to be measured and along which the fast neutron source is permitted to move over the lining in the direction of the thermal and epithermal neutron detector so as to be fixed in position within a certain distance from the thermal and epithermal neutron detector, determined by the original thickness of the lining.

It is further preferred to interpose the neutron moderator of the thermal and epithermal neutron detector between the thermal neutron counters arranged one above the other in relation to the lining portion subjected to thickness measurements, the thickness of the neutron moderator being determined by the original thickness of the lining and the energy of neutrons emitted by the fast neutron source.

It is further expedient that the immobilization of the fast neutron source with respect to the thermal and epithermal neutron detector should be effected by means of neutron moderating inserts occupying the vacant space inside the sealed housing of the lining thickness pulse transducer. It is desirable that the fast neutron source should be displayed by varying the respective locations of the neutron moderating inserts and the fast neutron source.

Finally, it is advantageous that the lining thickness pulse transducer should incorporate a fast neutron reflector of a neutron scattering material, rigidly coupled to the fast neutron source.

The present invention is basically advantageous in that the monitoring of the flux of neutrons scattered by the lining material and decelerated to thermal and epithermal energy levels ensures a high accuracy of lining thickness measurements, including measurements of original lining thicknesses, which applies to nearly every type of steel-making or calcining furnace.

The invention provides for a broader temperature range of the lining thickness pulse transducer, which mitigates the erstwhile stringent requirements imposed on its thermal insulation.

BRIEF DESCRIPTION OF THE ACCOMPANYING DRAWINGS

Other objects and advantages of the present invention will become more apparent from a consideration of the following detailed description of a preferred embodiment thereof, taken in conjunction with the accompanying drawings, wherein:

FIG. 2 is a section taken on line II—II of FIG. 1;

FIG. 3 is a general view of a device for gauging the thickness of refractory lining in accordance with the invention.

DETAILED DESCRIPTION OF THE INVENTION

Figure 1:
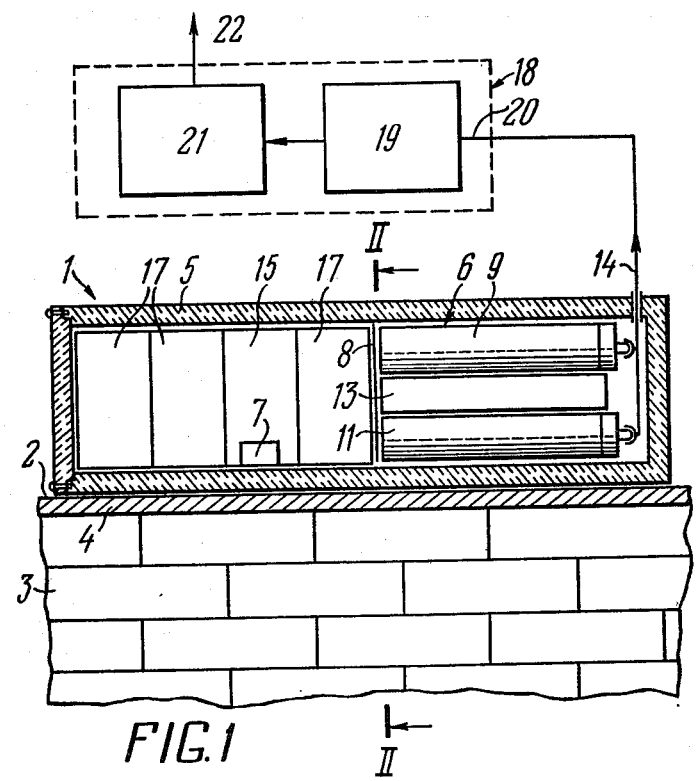
FIG. 1 is a structural diagram of a device for gauging the thickness of refractory lining in accordance with the invention, which presents an elevation view of the lining thickness pulse transducer.

According to the invention, the device for gauging the thickness of refractory lining comprises a lining thickness pulse transducer 1 (FIG. 1) mounted over a portion 2 of a lining 3 subjected to thickness measurements, on the external surface of a metal sheath 4 of a heating plant (not shown). The transducer 1 comprises a sealed housing 5 which accommodates a thermal and epithermal neutron detector 6 and a fast neutron source 7. Interposed between the detector 6 and fast neutron source 7 and arranged in immediate proximity to the detector 6 is a protective shield 8. The detector 6 incorporates neutron counters 9, 10, 11 and 12 (FIG. 2) and a neutron moderator 13 intended to expand the energy interval of neutrons counted by the counters 9, 10, 11 and 12. The moderator 13 is a plate the thickness of which is determined by the original thickness of the lining 3 and the energy of neutrons emitted by the source 7.

The counters 9, 10, 11 and 12 are arranged in two rows, one above the other, with respect to the portion 2 of the lining 3 so that there are two counters in each row. The moderator 13 is interposed between the counters 9 and 10 of the first row and counters 11 and 12 of the second row. The counters 9, 10, 11 and 12 are placed in parallel and have a single common output which serves as an output 14 (FIG. 1) of the transducer 1.

The source 7 is rigidly secured to a fast neutron reflector 15 of a neutron scattering material, such as graphite. The source 7 is mounted on that wall 16 of the housing 5 which is next to the portion 2 of the lining 3 and is movable over the portion 2 in the direction of the detector 6. While gauging the thickness of the lining 3, the source 7 can also be held in place. It is displaced and immobilized by neutron moderating inserts 17 occupying the vacant space inside the housing 5 of the transducer 1. The source 7 is stopped and fixed at a certain distance from the detector 6, which depends on the original thickness of the lining 3.

The output 14 of the transducer 1 is connected to an electric pulse measuring unit 18. The latter incorporates an electric pulse amplifier 19 whose input 20 serves as an input of the unit 18. The amplifier 19 is connected to an electric pulse counter 21 whose output 22 serves as an output of the unit 18 and an output of the device.

The unit 18 is adjusted by using a bar 23 (FIG. 3) to place the transducer 1 in a calibrating and checking attachment 24 which also serves as a container for transporting the transducer 1.

The device according to the invention operates as follows.

By moving the neutron moderating inserts 17 (FIG. 1) and fast neutron source 7, one selects a distance between the source 7 and detector 6, which accounts for a maximum change in the rate of count of thermal and epithermal neutrons, recorded by the unit 18, versus the thickness of the lining 3. The electric pulse measuring unit 18 is then checked and adjusted with the transducer 1 placed in the calibrating and checking attachment 24 (FIG. 3). This operation being over, the bar 23 is used to press the transducer 1 against the metal sheath 4 (FIG. 1). The source 7 emits fast neutrons which hit the lining 3. Some fast neutrons are directed towards the lining 3 by the fast neutron reflector 15. While passing through the lining 3, fast neutrons collide with nuclei of elements incorporated in the lining material, whereby they are scattered and decelerated. Some of these scattered and decelerated neutrons reach the thermal and epithermal neutron detector 6.

Those fast neutrons which the source 7 emits towards the detector 6 are moderated by the inserts 17 and absorbed by the protective shield 8.

Moderated by the material of the lining 3 and scattered neutrons are registered by the thermal neutron counters 9, 10, 11 and 12 (FIG. 2) as they reach the detector 6. Neutrons decelerated to thermal energy levels are registered by the counters 11 and 12 which are closer to the lining 3. The recording of thermal neutrons may be 100 percent effective, which means that thermal neutrons are fully absorbed by the counters 11 and 12. On the other hand, epithermal neutrons come through the counters 11 and 12 to reach the moderator 13 whereby they are decelerated to thermal energy levels to be recorded by all of the counters 9, 10, 11 and 12.

From the counters 9, 10, 11 and 12, electric pulses are applied through the output 14 of the transducer 1 to the electric pulse measuring unit 18. As these pulses are applied to the input 20 and amplified by the amplifier 19, they are recorded by the electric pulse counter 21. Thus the unit 18 records a certain number of pulses over a predetermined period of time. An operator converts this number of pulses to lining thickness by using some conventional method, such as the calibration curve technique.

On completion of the measurements, the transducer 1 is placed back in the container 24 (FIG. 3).

If there is no metal sheath 4 over the portion 2 (FIG. 1) where measurements are to be taken, the transducer 1 is applied directly to the lining 3.

The present invention makes it possible to employ a low-activity fast neutron source. This, in turn, makes it possible to produce a small-sized, radiologically safe lining thickness pulse transducer which can be serviced by a single operator.

The invention further makes it possible to take measurements at any point of a heating plant, which is accessible from the outside. If necessary, measurements can be taken through the metal sheath of the heating plant.

Finally, the invention makes it possible to rapidly check the state of refractory lining, which is one of the ways to ensure trouble-free operation of equipment over prolonged periods of time.

What is claimed is:

1. A device for gauging the thickness of a refractory lining of a heating plant, said refractory lining including a portion which is subjected to thickness measurement, said device comprising:

an electric pulse measuring unit having an input; and a lining thickness pulse transducer mounted on said portion of said refractory lining which is subjected to thickness measurements, said lining thickness pulse transducer having an output and being connected via said output to said input of said electric pulse measuring unit;

said lining thickness pulse transducer having a sealed housing including a wall adjoining said portion of said lining which is subjected to said thickness measurements;

said lining thickness pulse transducer including a fast neutron source accommodated in said sealed housing;

said lining thickness pulse transducer including a thermal and epithermal neutron detector accommodated in said sealed housing;

said lining thickness pulse transducer further including a protective shield accommodated in said sealed housing and interposed between said fast neutron source and said thermal and epithermal neutron detector;

said thermal and epithermal neutron detector further including thermal neutron counters in a number determined by the activity of said fast neutron source;

said thermal and epithermal neutron detector further comprising a neutron moderator intended to expand the energy intervals of neutrons counted by said thermal neutron counters.

2. A device as claimed in claim 1, wherein said fast neutron source is arranged on said wall of said sealed housing of said lining thickness pulse transducer so as to be able to move over that wall in the direction of said thermal and epithermal neutron detector and rendered immobile so as to be held in place at a distance, from said thermal and epithermal neutron detector, which distance is determined by the original thickness of said lining.

3. A device as claimed in claim 2, wherein said lining thickness pulse transducer incorporates a fast neutron reflector of a neutron scattering material, which is rigidly coupled to said fast neutron source.

4. A device for gauging the thickness of a refractory lining of a heating plant, said refractory lining including a portion which is subjected to thickness measurement, said device comprising:

an electric pulse measuring unit having an input; and a lining thickness pulse transducer mounted on said portion of said refractory lining which is subjected to thickness measurements, said lining thickness pulse transducer having an output and being connected via said output to said input of said electric pulse measuring unit;

said lining thickness pulse transducer having a sealed housing including a wall adjoining said portion of said lining which is subjected to said thickness measurements;

said lining thickness pulse transducer including a fast neutron source accommodated in said sealed housing;

said lining thickness pulse transducer including a thermal and epithermal neutron detector accommodated in said sealed housing;

said lining thickness pulse transducer further including a protective shield accommodated in said sealed housing and interposed between said fast neutron source and said thermal and epithermal neutron detector;

said thermal and epithermal neutron detector further including thermal neutron counters in a number determined by the activity of said fast neutron source;

said thermal and epithermal neutron detector further comprising a neutron moderator intended to expand the energy intervals of neutrons counted by said thermal neutron counters;

wherein said neutron moderator of said thermal and epithermal neutron detector is interposed between said thermal neutron counters arranged one above the other in relation to said portion of said lining where thickness measurements are taken, the thickness of said neutron moderator being determined by the original thickness of said lining and the energy of neutrons emitted by said fast neutron source.

5. A device as claimed in claim 4, wherein said fast neutron source is rendered immobile and held in place with respect to said thermal and epithermal neutron detector by means of neutron moderating inserts occupying the vacant space inside said sealed housing of said lining thickness pulse transducer.

6. A device as claimed in claim 4, wherein said fast neutron source is displaced by varying the respective locations of said neutron moderating inserts and said fast neutron source.

7. A device as claimed in claim 4, wherein said lining thickness pulse transducer incorporates a fast neutron reflector of a neutron scattering material, which is rigidly coupled to said fast neutron source.

8. A device for gauging the thickness of a refractory lining of a heating plant, said refractory lining including a portion which is subjected to thickness measurement, said device comprising:

an electric pulse measuring unit having an input; and a lining thickness pulse transducer mounted on said portion of said refractory lining which is subjected to thickness measurements, said lining thickness pulse transducer having an output and being connected via said output to said input of said electric pulse measuring unit;

said lining thickness pulse transducer having a sealed housing including a wall adjoining said portion of said lining which is subjected to said thickness measurements;

said lining thickness pulse transducer including a fast neutron source accommodated in said sealed housing;

said lining thickness pulse transducer including a thermal and epithermal neutron detector accommodated in said sealed housing;

said lining thickness pulse transducer further including a protective shield accommodated in said sealed housing and interposed between said fast neutron source and said thermal and epithermal neutron detector;

said thermal and epithermal neutron detector further including thermal neutron counters in a number determined by the activity of said fast neutron source;

said thermal and epithermal neutron detector further comprising a neutron moderator intended to expand the energy intervals of neutrons counted by said thermal neutron counters;

wherein said fast neutron source is arranged on said wall of said sealed housing of said lining thickness pulse transducer so as to be able to move over that wall in the direction of said thermal and epithermal neutron detector and rendered immobile so as to be held in place at a distance, from said thermal and epithermal neutron detector, which distance is determined by the original thickness of said lining;

wherein said neutron moderator of said thermal and epithermal neutron detector is interposed between said thermal neutron counters arranged one above the other in relation to said portion of said lining where thickness measurements are taken, the thickness of said neutron moderator being determined by the original thickness of said lining and the energy of neutrons emitted by said fast neutron source.

9. A device for gauging the thickness of a refractory lining of a heating plant, said refractory lining including a portion which is subjected to thickness measurement, said device comprising:

an electric pulse measuring unit having an input; and a lining thickness pulse transducer mounted on said portion of said refractory lining which is subjected to thickness measurements, said lining thickness pulse transducer having an output and being connected via said output to said input of said electric pulse measuring unit;

said lining thickness pulse transducer having a sealed housing including a wall adjoining said portion of said lining which is subjected to said thickness measurements;

said lining thickness pulse transducer including a fast neutron source accommodated in said sealed housing;

said lining thickness pulse transducer including a thermal and epithermal neutron detector accommodated in said sealed housing;

said lining thickness pulse transducer further including a protective shield accommodated in said sealed housing and interposed between said fast neutron source and said thermal and epithermal neutron detector;

said thermal and epithermal neutron detector further including thermal neutron counters in a number determined by the activity of said fast neutron source;

said thermal and epithermal neutron detector further comprising a neutron moderator intended to expand the energy intervals of neutrons counted by said thermal neutron counters;

wherein said fast neutron source is arranged on said wall of said sealed housing of said lining thickness pulse transducer so as to be able to move over that wall in the direction of said thermal and epithermal neutron detector and rendered immobile so as to be held in place at a distance, from said thermal and epithermal neutron detector, which distance is determined by the original thickness of said lining;

wherein said fast neutron source is rendered immobile and held in place with respect to said thermal and epithermal neutron detector by means of neutron moderating inserts occupying the vacant space inside said sealed housing of said lining thickness pulse transducer.

10. A device as claimed in claim 9, wherein said fast neutron source is displaced by varying the respective locations of said neutron moderating inserts and said fast neutron source.

11. A device as claimed in claim 9, wherein said lining thickness pulse transducer incorporates a fast neutron reflector of a neutron scattering material, which is rigidly coupled to said fast neutron source.

12. A device for gauging the thickness of a refractory lining of a heating plant, said refractory lining including a portion which is subjected to thickness measurement, said device comprising:

an electric pulse measuring unit having an input; and a lining thickness pulse transducer mounted on said portion of said refractory lining which is subjected to thickness measurements, said lining thickness pulse transducer having an output and being connected via said output to said input of said electric pulse measuring unit;

said lining thickness pulse transducer having a sealed housing including a wall adjoining said portion of said lining which is subjected to said thickness measurements;

said lining thickness pulse transducer including a fast neutron source accommodated in said sealed housing;

said lining thickness pulse transducer including a thermal and epithermal neutron detector accommodated in said sealed housing;

said lining thickness pulse transducer further including a protective shield accommodated in said sealed housing and interposed between said fast neutron source and said thermal and epithermal neutron detector;

said thermal and epithermal neutron detector further including thermal neutron counters in a number determined by the activity of said fast neutron source;

said thermal and epithermal neutron detector further comprising a neutron moderator intended to expand the energy intervals of neutrons counted by said thermal neutron counters;

wherein said fast neutron source is arranged on said wall of said sealed housing of said lining thickness pulse transducer so as to be able to move over that wall in the direction of said thermal and epithermal neutron detector and rendered immobile so as to be held in place at a distance, from said thermal and epithermal neutron detector, which distance is determined by the original thickness of said lining;

wherein said fast neutron source is displaced by varying the respective locations of said neutron moderating inserts and said fast neutron source.

13. A device as claimed in claim 12, wherein said lining thickness pulse transducer incorporates a fast neutron reflector of a neutron scattering material, which is rigidly coupled to said fast neutron source.

* * * * *